(12) United States Patent
Chiang

(10) Patent No.: US 6,830,124 B2
(45) Date of Patent: Dec. 14, 2004

(54) EAR PLUG

(76) Inventor: Herman Chiang, 11F-2 No. 634-9 Ching-Ping RD., Chung-Ho City, Taipei Hsien (TW)

( * ) Notice: Subject to any disclaimer, the term of this patent is extended or adjusted under 35 U.S.C. 154(b) by 0 days.

(21) Appl. No.: 10/420,853

(22) Filed: Apr. 23, 2003

(65) Prior Publication Data

US 2004/0211621 A1 Oct. 28, 2004

(51) Int. Cl.[7] .......................... A61B 7/02; H04R 25/02; A61F 11/08
(52) U.S. Cl. ..................... 181/135; 181/130; D24/106; 128/864
(58) Field of Search .................. 181/135, 130, 181/129; D24/106; 128/864; 381/380, 68.6

(56) References Cited

U.S. PATENT DOCUMENTS

| | | | | |
|---|---|---|---|---|
| 1,355,276 A | * | 10/1920 | Schultz | 128/864 |
| D98,095 S | * | 1/1936 | Steckler | D24/106 |
| 2,070,403 A | * | 2/1937 | Hershman | 128/864 |
| 3,259,128 A | * | 7/1966 | Leight | 128/865 |
| 3,415,246 A | * | 12/1968 | Hill | 128/864 |
| 4,094,315 A | * | 6/1978 | Leight | 128/864 |
| 4,540,063 A | * | 9/1985 | Ochi et al. | 181/135 |
| 4,564,009 A | * | 1/1986 | Brinkhoff | 128/864 |
| 5,319,163 A | * | 6/1994 | Scott | 181/130 |
| 5,881,729 A | * | 3/1999 | Castillo | 128/864 |
| D408,526 S | * | 4/1999 | Westerdal | D24/106 |
| D414,260 S | * | 9/1999 | Conner | D24/106 |
| 6,129,175 A | * | 10/2000 | Tutor et al. | 181/135 |

FOREIGN PATENT DOCUMENTS

DE  3304362 A1 * 8/1984 ........... A61F/11/00

* cited by examiner

*Primary Examiner*—David Martin
*Assistant Examiner*—Edgardo San Martin
(74) *Attorney, Agent, or Firm*—Troxell Law Office PLLC

(57) ABSTRACT

An ear plug includes a first shelter for extending into an ear canal thereby preventing water from flowing into an inner ear a second shelter for accommodating with the ear canal thereby preventing water from flowing into the ear canal, and a connection portion is narrower than those of the first and second shelters connected between the first and second shelters. The first shelter has a flexible and thin peripheral flange. The second shelter has first and second walls that defines a hollow cylindrical. The first wall of the second shelter is connected with the connection portion. The second shelter and the connection portion are also hollow.

6 Claims, 5 Drawing Sheets

EAR PLUG

BACKGROUND OF THE INVENTION

1. Field of the Invention

The present invention relates to an ear plug, and particularly to an ear plug for swimming to prevent water from flowing into an ear.

2. Related Art

A conventional ear plug for swimming to prevent water from flowing into ears is generally made of foam or silicone by integral molding and is solid. FIGS. 1–3 show a conventional ear plug 1 formed of silicone by integral molding. The ear plug 1 has a solid body 10, a taper head 11 at one end of the body 10, first and second thin shelters 12, 13 peripherally extending from the body 10. The head 11, and the first and second shelters 12, 13 are generally equally spaced and are extendable into an ear thereby preventing water from flowing into the ear. The head 11 has a slightly smaller diameter than an ear canal 20. The head 11 is solid and thick and so rigid relatively for extending into a middle ear 21. The first shelter 12 is thinner than the second shelter 13 for interfered extending into the ear canal 20. The second shelter 13 has a larger diameter than the first shelter 12 for stopping the ear canal 20.

However, the ear plug 1 is uncomfortable to wear since the first shelter 12 is inserted into the middle ear 21 over interference. Moreover, during the wearing of the ear plug 1, air in the middle ear is compressed into an inner ear. When the ear plug 1 is being taken off, air pressure tends to keep the ear plug 1 in the ear canal 20 due to air pressure difference between inside and outside of the ear canal 20. So the ear plug 1 is easy to hurt the eardrum.

Furthermore, a user can not hear other people when wearing the ear plug 1. So, it is not convenient to communicate with others when wearing the ear plug 1.

SUMMARY OF THE INVENTION

Accordingly, an object of the present invention is to provide an ear plug for swimming which is comfortable to wear and is safe from hurting a user's eardrum.

Another object of the present invention is to provide an ear plug for swimming which is hollow for keeping a user hearable when wearing the ear plug.

To achieve the above-mentioned objects, an ear plug in accordance with the present invention includes a first shelter for extending into an ear canal thereby preventing water from flowing into the ear canal, a second shelter for accommodating with the ear canal thereby preventing water from flowing into the ear canal, and a connection portion connected between the first and second shelters. The first shelter has a flexible and thin peripheral flange. The second shelter has first and second walls connected with each other. The first wall of the second shelter is connected with the connection portion. The second shelter and the connection portion are hollow.

Other objects, advantages and novel features of the present invention will be drawn from the following detailed embodiment of the present invention with attached drawings.

DESCRIPTION OF THE PREFERRED EMBODIMENTS

A pair of ear plugs of the present invention includes left and right ear plugs for respectively extending into left and right ears. Structures of the left and right ear plugs are symmetrical. So, only the right ear plug is detailedly described hereinafter for illustration of the present invention.

Figure 1:
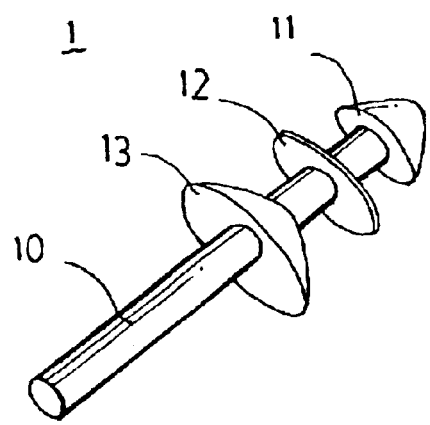
FIG. 1 is a perspective view of a conventional ear plug.
Figure 2:
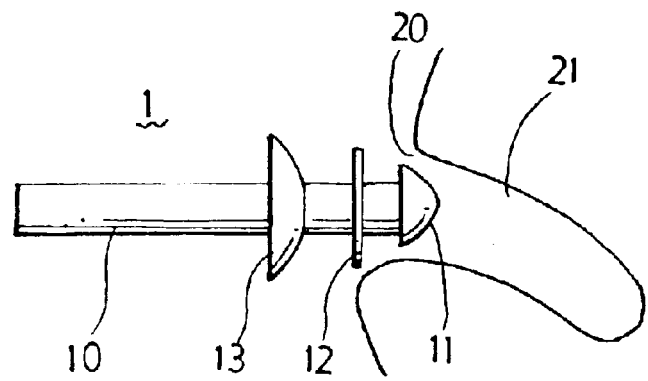
FIG. 2 is a schematic view showing the ear plug of FIG. 1 to extend into an ear canal.
Figure 3:
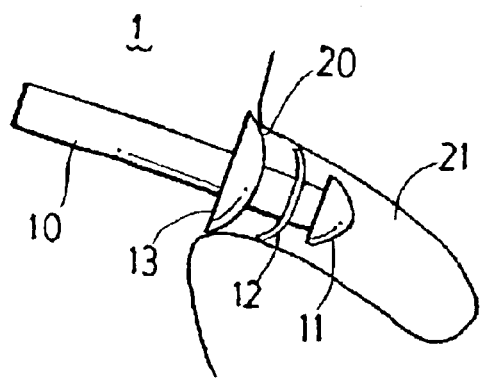
FIG. 3 is similar to FIG. 2 but showing the ear plug extended into the ear canal.
Figure 4:
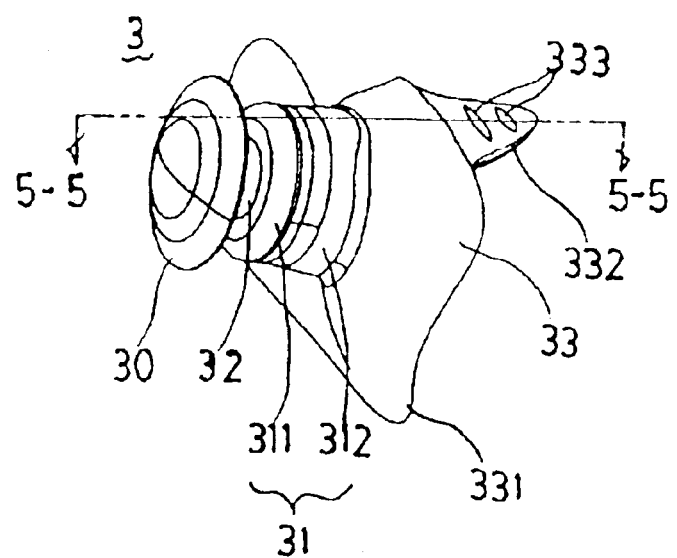
FIG. 4 is a perspective view of a right ear plug in accordance with an embodiment of the present invention.
Figure 5:
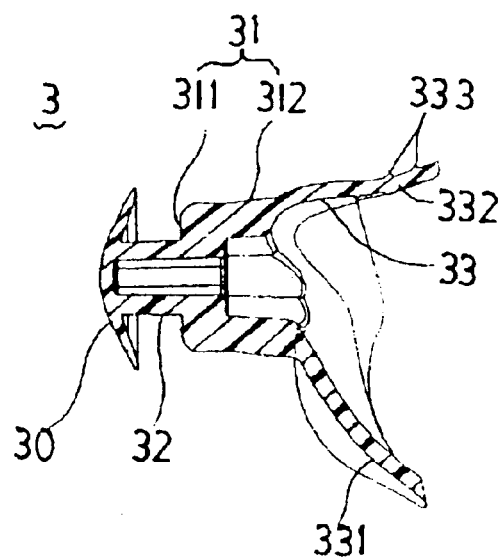
FIG. 5 is a cross-sectional view taken along line 5—5 in FIG. 4.
Figures 6, 7:
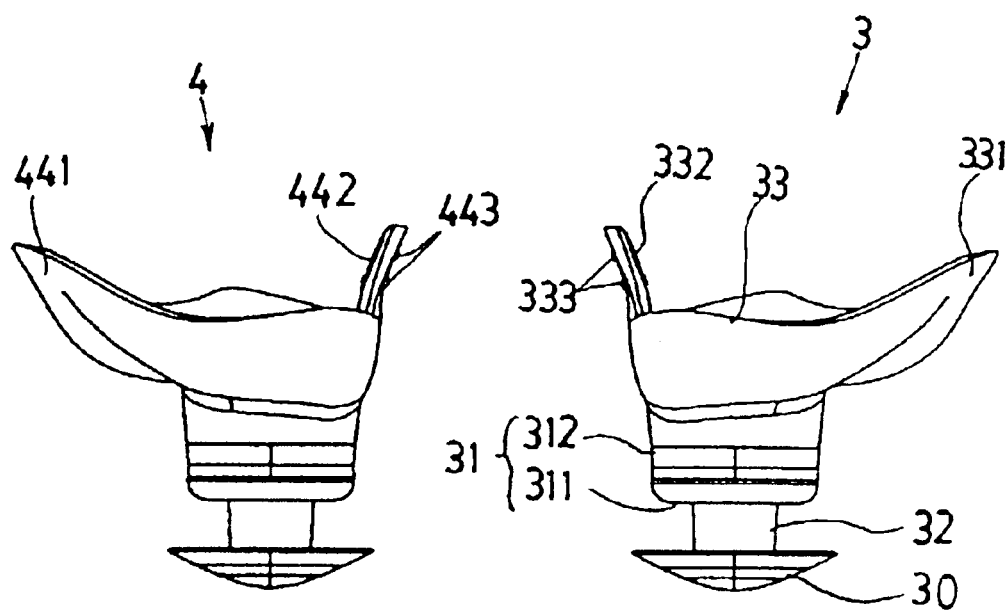
FIG. 6A is a top plan view of the right ear plug.
FIG. 6B is a rear elevational view of the right ear plug.
FIG. 7A is a top plan view of a left ear plug in accordance with an embodiment of the present invention.
FIG. 7B is a rear elevational view of the left ear plug.
Figures 6, 7:
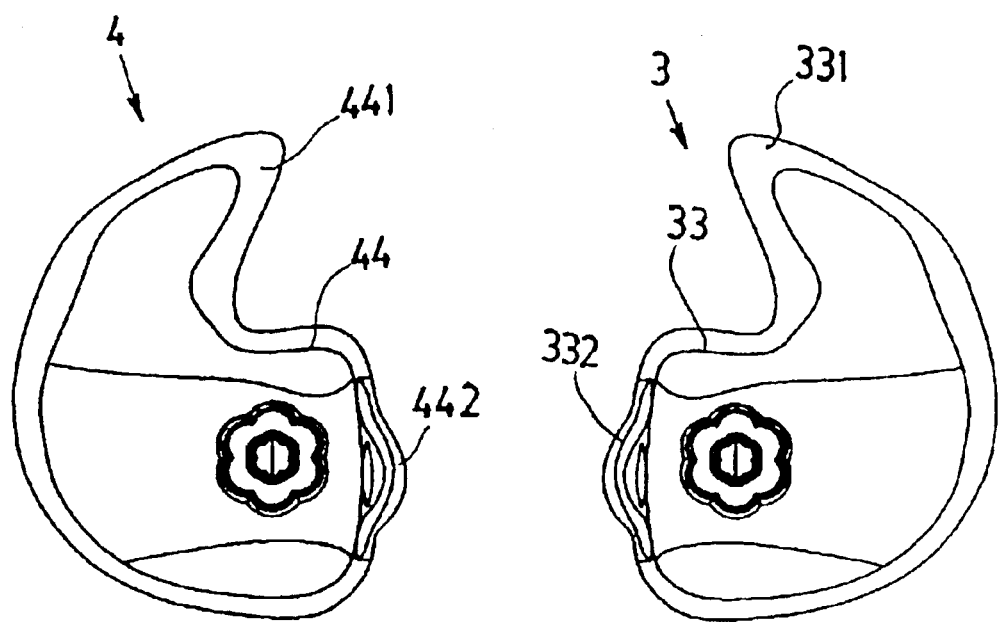
Figure 8:
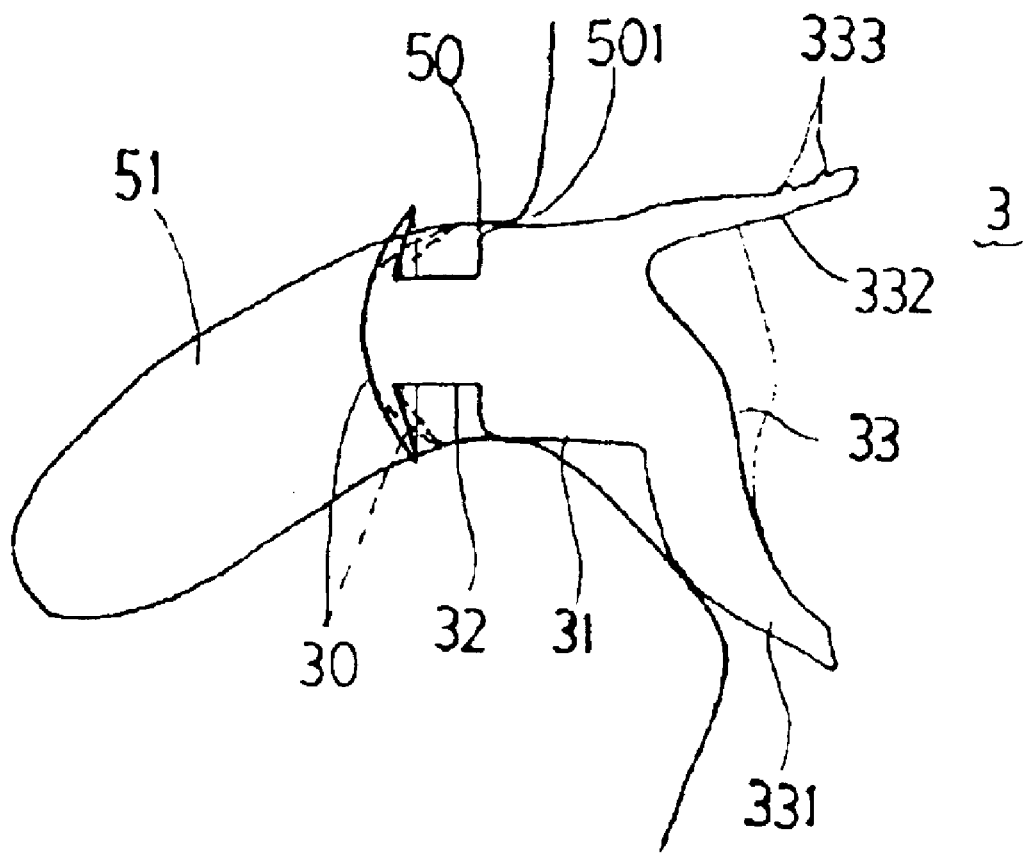
FIG. 8 is a schematic view showing the ear plug of FIG. 4 extended into an ear canal.

Referring to FIGS. 4, 5 and 8, a right ear plug 3 of the present invention integrally made of rubber is hollow with a central slot (not labeled) and includes a first shelter 30, a second shelter 31, a connection portion 32 connected between the first and second shelters 30, 31, and a tail portion 33 peripherally extending from the second shelter 31 to conform to the shape of a periphery of antihelix of an ear. The central slot extends from the tail portion 33 to the first shelter 30 in this embodiment. The central slot also can extend from the tail portion 33 to the connection portion 32. The first and second shelters 30, 31 and the connection portion 32 are flexible due to the central slot of the ear plug 3. The first shelter 30 is arcuate with a flexible and thin peripheral flange for extending into an ear canal 50 thereby preventing water from flowing into an inner ear. Thickness of the flange of the first shelter 30 is 0.4 mm in this embodiment to provide flexibility. Diameter of the thin peripheral flange of the first shelter 30 is slightly wider than that of the ear canal 50.

The connection portion 32 has a narrower diameter than those of the first and second shelters 30, 31. A receiving space is defined between the first and second shelters 30, 31 for receiving the flange of the first shelter 30 when the first shelter 30 extends into the ear canal 50.

The second shelter 31 has a narrower diameter than the first shelter 30 for accommodating with the ear canal 50 thereby preventing water from flowing into the ear canal 50. The thickness of the connection portion 32 is thicker than that of the flange of the first shelter 30 but thiner r than that of the second shelter 31. The second shelter 31 includes a first wall 311 connected to the connection portion 32 and a second wall 312 connected with the first wall 311. The first wall 311 is narrower than that of the thin peripheral flange of the first shelter 30. The second wall 312 is generally cylindrical and is flexible for accommodation with different sizes of ear canal. The second wall 312 is also thicker than that of the first shelter 30.

Also referring to FIGS. 6A, 6B, 7A and 7B, the tail portion 33 extends from the second wall 312 of the second shelter 31 and is bell-mouthed for accommodating with periphery of the ear canal 50 thereby enhancing to prevent water from flowing into the ear canal 50. The tail portion 33 includes a guide portion 331 and a handle 332 extending from the tail portion 33. The guide portion 331 is able to conform to the shape of an external auditory canal thereby assuring that the ear plug 3 extends into the ear canal 50 at a given depth and enhancing to prevent water from flowing into the ear canal 50. The guide portion 331 also prevents the ear plug 3 from extending into the ear canal 50 so deep as to hurt an eardrum. In other words, the guide portion 331 assures the ear plug 3 extends into the ear canal 50 at a given depth.

FIGS. 6A, 6B, 7A and 7B show right and left ear plugs 3, 4 with tail portions 33, 44 having guide portions 331, 441 and handles 332, 442. The guide portion 331 of the right ear plug 3 locates at the right side of the right ear plug 3. Similarly, the guide portion 441 of the left ear plug 4 locates at the left side of the left ear plug 4. The handles 332, 442 shall be different direction that located near a tragus of an ear by a left ear or right ear. A plurality of protrusions 333, 443 is formed at the handles 332, 442 for easy to hold.

Referring to FIG. 8, in use, the handle 332 of the right ear plug 3 is hold to insert the first and second shelters 30, 31 into the ear canal 50 in sequence. As shown in dashed line, the thin peripheral flange of the first shelter 30 is ready to be deflected to receive in the receiving space between the first and second shelters 30, 31. The second shelter 31 is accommodated with the ear canal 50. The guide portion 331 is accommodated with periphery of antihelix of the ear. Therefore, the ear plug 3 is preventable water from flowing into the ear canal 50. Due to the flexibility of the first and second shelters 30, 31, the ear plug 3 is comfortable to wear. The ear plug 3 is extended into the ear canal 50 at a short given depth and the guide portion 331 prevents the ear plug 3 from extending deep into a middle ear 51. Thus, air pressure difference between inside and outside of ear canal 50 is so slight that the ear plug 3 is safe from hurting a user's eardrum. Furthermore, since the air plug 3 is hollow and just extends into the ear canal 50 at a short given depth, a user is hearable when wearing the ear plugs 3, 4 whereby the user can communicate with others without taking off the ear plugs 3, 4.

Figure 9:
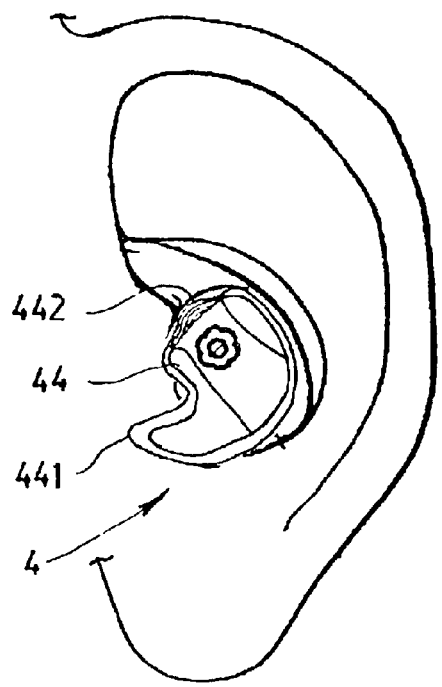
FIG. 9A is a schematic view showing a left ear wearing the left ear plug.
FIG. 9B is a schematic view showing a right ear wearing the right ear plug.
Figure 9:
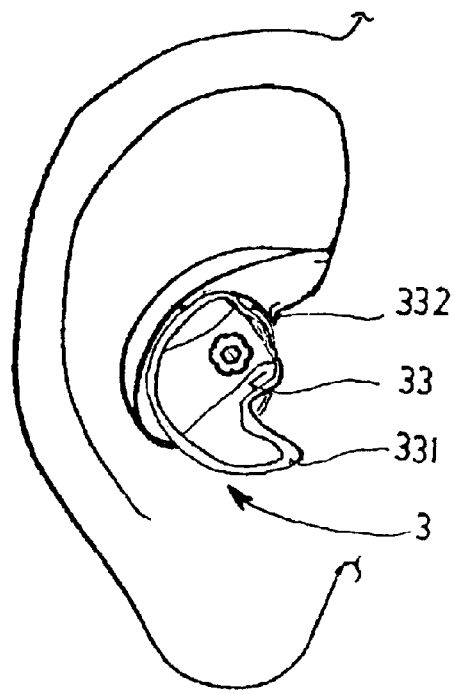

Referring to FIGS. 9A and 9B, the right and left ear plugs 3, 4 are worn in right and left ear canals. The guide portion 331 of the right ear plug 3 is accommodated with the external auditory canal of the right ear and covers the right ear canal, thereby enhancing to preventing water from flowing into the ear canal. Likewise, the guide portion 441 of the left ear plug 4 is accommodated with the external auditory canal of the left ear and covers the left ear canal, thereby enhancing to preventing water from flowing into the ear canal.

It is understood that the invention may be embodied in other forms without departing from the spirit thereof. Thus, the present example and embodiment are to be considered in all respects as illustrative and not restrictive, and the invention is not to be limited to the details given herein.

What is claimed is:

1. An ear plug comprising:

a first shelter for insertion into an ear canal thereby preventing water from flowing into an inner ear, the first shelter having a flexible and thin peripheral flange;

a second shelter having a first wall and a second wall that defines a hollow cylinder to be inserted into the ear canal thereby preventing water from flowing into the ear canal; and a connection portion connected between the first shelter and the first wall of the second shelter, the connection portion being hollow wherein a diameter of the connection portion is less than those of the first and second shelters, wherein a tail portion extends from the second wall of the second shelter and is bell-mouth shaped to conform to a shape of a periphery of an antihelix of an outer ear to prevent water from flowing into the ear canal, wherein the tail portion includes a guide portion conforming to a shape of an external auditory canal and limiting a depth to which the ear plug extends into the ear canal to prevent harm to an eardrum, and preventing water from flowing into the ear canal.

2. The ear plug as claimed in claim 1, further comprising a handle extending from the tail portion and positioned adjacent to a tragus of an ear, the handle shaped for one of a left ear, and a right ear.

3. The ear plug as claimed in claim 2, wherein the thickness of the flange of the first shelter is 0.4 mm.

4. The ear plug as claimed in claim 3, wherein the thickness portion is thicker than that of the thin peripheral flange of the first than that of the second shelter.

5. The ear plug as claimed in claim 3, wherein a plurality of protrusions are formed at the handle of the tail portion.

6. The ear plug as claimed in claim 1, wherein the diameter of the thin peripheral flange of the first shelter is wilder than that of the diameter of the ear canal for extending into the ear canal.

* * * * *